(12) United States Patent
Sbragia et al.

(10) Patent No.: US 10,499,842 B2
(45) Date of Patent: Dec. 10, 2019

(54) CLINICAL ASSESSMENT OF BALANCE ON A PLATFORM WITH CONTROLLED STABILITY

(71) Applicant: Diversified Healthcare Development, LLC, Fallbrook, CA (US)

(72) Inventors: Dean G. Sbragia, Fallbrook, CA (US); John F. Byrd, Independence, VA (US)

(73) Assignee: Diversified Healthcare Development, LLC, Fallbrook, CA (US)

( * ) Notice: Subject to any disclaimer, the term of this patent is extended or adjusted under 35 U.S.C. 154(b) by 168 days.

(21) Appl. No.: 15/276,951

(22) Filed: Sep. 27, 2016

(65) Prior Publication Data

US 2018/0085044 A1    Mar. 29, 2018

(51) Int. Cl.
*A61B 5/00* (2006.01)
*A61B 5/103* (2006.01)

(52) U.S. Cl.
CPC .......... *A61B 5/4023* (2013.01); *A61B 5/1036* (2013.01); *A61B 2562/0247* (2013.01); *A61B 2562/168* (2013.01)

(58) Field of Classification Search
CPC ....... A61B 5/11; A61B 5/1124; A61B 5/1036; A61B 5/4023; A61B 2562/168; A61B 2562/0247
See application file for complete search history.

(56) References Cited

U.S. PATENT DOCUMENTS

| | | | |
|---|---|---|---|
| 2,670,729 A | 3/1954 | Grant | |
| 3,859,736 A | 1/1975 | Hill et al. | |
| 3,906,931 A | 9/1975 | Terekhov | |
| 4,509,743 A | 4/1985 | Lie | |
| 4,738,260 A | 4/1988 | Nashner | |
| 5,052,406 A | 10/1991 | Nashner | |
| 5,112,045 A | 5/1992 | Mason et al. | |

(Continued)

OTHER PUBLICATIONS

Sharma, R., Romi, S.N. and Srivastava, R.K., An Objective Approach for Assessment of Balance Disorders and Role of Visual Balance Feedback Training in the Treatment of Balance Disorders: A Preliminary Study, IJPMR 12, Apr. 2001: 25-30,www.iapmr.org/ijpmr/ijpmr01/200105.pdf.

(Continued)

*Primary Examiner* — Max F Hindenburg
(74) *Attorney, Agent, or Firm* — Gibb & Riley, LLC

(57) ABSTRACT

Systems and methods for clinical assessment of balance may include a tilting balance platform further including: an upper platform, a lower platform, and an array of force transducers sandwiched between the upper platform and the lower platform. The systems may also include: a toroidal bladder supporting the lower platform; an air pressure sensor and a control valve connected to the toroidal bladder; an inclinometer that measures tilt information of the balance platform; and a computer that receives a control signal to activate one of: the array of force transducers and the inclinometer. If the array of force transducers is activated, then a clinical test is performed to measure changes to a subject's Center of Pressure on a stabilized balance platform, and if the inclinometer is activated, then another clinical test is performed to measure the tilt information caused by a subject's movements on a de-stabilized balance platform.

5 Claims, 8 Drawing Sheets

(56) References Cited

U.S. PATENT DOCUMENTS

| | | | |
|---|---|---|---|
| 5,627,327 A | 5/1997 | Zanakis | |
| 5,830,158 A | 11/1998 | Zanakis | |
| 5,919,150 A | 7/1999 | Zanakis | |
| 5,980,429 A | 11/1999 | Nashner | |
| 6,389,883 B1 | 5/2002 | Berme et al. | |
| 6,575,885 B1 | 6/2003 | Week et al. | |
| 7,179,234 B2 | 2/2007 | Nashner | |
| 7,219,449 B1 * | 5/2007 | Hoffberg | A43B 1/0054 36/29 |
| 7,686,396 B2 * | 3/2010 | Schaaf | A47C 7/14 297/313 |
| 8,529,418 B2 | 9/2013 | Stewart et al. | |
| 8,704,855 B1 | 4/2014 | Berme et al. | |
| 2006/0030795 A1 | 2/2006 | Luberski et al. | |
| 2006/0264786 A1 | 11/2006 | Nashner | |
| 2007/0184953 A1 | 8/2007 | Luberski et al. | |
| 2007/0208278 A1 | 9/2007 | Kohen-Raz | |
| 2007/0270296 A1 | 11/2007 | Caldicott | |
| 2008/0228110 A1 | 9/2008 | Berme | |
| 2010/0075808 A1 | 3/2010 | Luberski et al. | |
| 2012/0231931 A1 | 9/2012 | Luberski et al. | |
| 2014/0081177 A1 | 3/2014 | Eguibar | |

OTHER PUBLICATIONS

Mancini, M. and Horak, F.B., The relevance of clinical balance assessment tools to differentiate balance deficits, Eur J Phys Rehabil Med. Jun. 2010: 46(2): 239-248.

Owner's Instructions & Assembly of the Korebalance® System, Medical Fitness Solution, Mar. 17, 2015.

* cited by examiner

CLINICAL ASSESSMENT OF BALANCE ON A PLATFORM WITH CONTROLLED STABILITY

BACKGROUND

Field of the Invention

The present invention relates to a system and method for clinically assessing balance of a subject on a balance platform with controlled stability.

Description of Related Art

FIG. 1A and FIG. 1B illustrate a cross section and a top view, respectively, of a system for the clinical assessment of balance 100 that responds to movements of a subject standing on a rigid balance platform 106 by tilting in any of the directions of the horizontal plane. As depicted in the cross section of FIG. 1A, which corresponds to the centerline A-A' of FIG. 1B, and in the top view of FIG. 1B, where the balance platform 106 is removed for illustrative purposes, a ball joint 112, supporting the balance platform 106, is disposed on a vertical support 118 underneath the center of the balance platform 106. A toroidal bladder 124, made of an elastic material that can be inflated and deflated, and the vertical support 118 are disposed on a base 130. The toroidal bladder 124 encircles the vertical support 118 and supports the periphery of the undersurface of the balance platform 106. Inflation of the toroidal bladder 124, by an air pump 136 through a control valve 142, restrains downward tilting of the balance platform 106 and provides greater stability to the balance platform 106; while deflation of the toroidal bladder 124, by venting to the atmosphere through the control valve 142, facilitates downward tilting of the balance platform 106 and provides lesser stability to the balance platform 106.

A real time electronic inclinometer 148, disposed on the undersurface of the balance platform 106, detects the direction of tilt of the balance platform 106 in the horizontal x-y plane when supported by the ball joint 112 and the degree of tilt of the balance platform 106 relative to the vertical z-axis. A computer 164, connected to the electronic inclinometer 148, receives the direction and degree of tilt of the balance platform 106 and displays this tilt information on a monitor 168 in real time.

The computer 164 is also connected to an air pressure sensor 156 that measures an air pressure of the toroidal bladder 124 in real time. During the course of many clinical tests, several air pressures are entered into the computer 164 by a clinician to either increase or decrease air pressure within the toroidal bladder 124. To increase air pressure within the toroidal bladder 124, the computer 164 activates the air pump 136, forcing air into the toroidal bladder 124 via the control valve 142; while, to decrease air pressure, the computer 164 vents the toroidal bladder 124 to the atmosphere via the control valve 142.

Another system for the diagnosis of abnormalities in balance correction responses comprises a servo-mechanical apparatus that moves two support surfaces, upon which the subject stands, by either an anterior/posterior rotation about a transverse axis, or a horizontal anterior/posterior translation of the support surfaces. Force sensing means within the two support surfaces and optional body position and motion sensing means provide measurements functionally related to displacement of the subject from the assumed equilibrium position. The system processor also provides three balance correction response measurements in response to changes of the displacement of the support surfaces. The three correction response measurements include: 1) a calculated center of foot pressure derived from force transducer measurements embedded in the support surfaces, 2) body sway derived from velocity transducers attached to the upper torso of the subject, and 3) muscular reactions derived from pairs of electromyographic electrodes placed over muscles on the left and right sides of the subject. Additionally, a visual image can be projected on the subject's eyes. Movement of the support surfaces perturbs the subject's stance producing a balance correction response, allowing a differential diagnosis of abnormalities for balance correction responses by the subject to be determined, based on the changes to the center of foot pressure, changes in body sway, and electromyographic reactions.

Yet another system for the clinical assessment of balance comprises a force measurement system that receives measurements from a force plate or dual force plates upon which a subject stands. The force plate(s) can be controllably translated forward or backward by an electrically powered screw shaft or rotated about a transverse axis by a pivot arm connected to another electrically powered screw shaft. Movements by the subject upon the force plate(s) result in forces that are instantaneously measured by a quadrilateral array of force transducers or by a pair of opposing transducer beams that are positioned underneath the force plate(s). The force transducers are connected to a controller that converts the measured forces to components including a vertical force, $F_z$, a left/right force, $F_x$, and a forward/back force, $F_y$. A computer then computes a center of gravity (COG) or center of pressure (COP) based on the force components. The subject's height, entered into the system at an operator's console, and the computed COG or COP are used to calculate the sway angle of the subject. The system also includes a projected hemispherical visual display of a three-dimensional image that fully encompasses the subject's field of view.

During various clinical protocols to assess the contributions of a subject's visual inputs, somatosensory inputs, and vestibular inputs to maintain balance, the three-dimensional (3D) image projected on the hemispherical visual display may be synchronized with the calculated sway angle of the subject. In one aspect of a Sensory Organization Test (SOT), the force plate(s) remains stationary, while the 3D image projected on the hemispherical visual display is synchronized with the computed sway angle of the subject, to suppress visual cues to the subject's sway. In another aspect of the SOT, rotation of the force plate(s) about the transverse axis may be synchronized with the computed subject's sway, while a stationary three-dimensional image is projected on the hemispherical visual display, providing visual cues to the subject's sway. Finally, in yet another aspect of the SOT, both the 3D image projected on the hemispherical visual display and the rotation of the force plate(s) about the transverse axis may be synchronized with the computed subject's sway, to reduce the visual and somatosensory cues to the subject's sway.

SUMMARY

In view of the foregoing, an embodiment of the disclosure may provide a system for clinical assessment of balance. The system may include a balance platform supported under its center by a ball joint, where the ball joint disposed atop a vertical support, which in turn is disposed on a base. The system may also include a toroidal bladder that supports the balance platform under its periphery, encircles the vertical support, and is disposed on the base. The system may further include a high-pressure reservoir that maintains a range of high air pressures, in which a lowest value of the range of high air pressures exceeds that of a maximum target air pressure for the toroidal bladder. The system may yet further include a control valve that is connected to the high-pressure reservoir, the toroidal bladder, and the atmosphere. The system may yet further include an air pressure sensor connected to the toroidal bladder. Finally, the system may include a computer that receives an air pressure value from the air pressure sensor, sends a first control signal to open the control valve between the high-pressure reservoir and the toroidal bladder inflating the toroidal bladder to a target air pressure, when an air pressure value of the toroidal bladder is less than the target air pressure, and sends a second control signal to close the control valve, when the air pressure sensor senses the target air pressure in the toroidal bladder.

Another embodiment of the disclosure may provide a method of performing a clinical assessment of balance. The method may include selecting a clinical test, characterized by a pre-determined sequence of binary questions, from a test mode of a system for the clinical assessment of balance. The system may include: a balance platform supported at its center by a ball joint; a toroidal bladder supporting the balance platform under its periphery; an air pressure sensor and a control valve connected to the toroidal bladder; an inclinometer, disposed on an underside of the balance platform, measuring tilt information of the balance platform in real time; a computer that receives a sensed air pressure of the toroidal bladder from the air pressure sensor, sends one of: a first control signal to the control valve to inflate the toroidal bladder when the sensed air pressure is less than a target air pressure, and a second control signal to the control valve to deflate the toroidal bladder when the sensed air pressure is greater than the target air pressure, and receives the tilt information from the inclinometer; and a monitor that displays the tilt information in real time. The method may also include displaying on the monitor a first binary question of the pre-determined sequence of binary questions. The method may further include responding to the first binary question of the system with one of: a first affirmative response and a first negative response. The method may yet further include displaying on the monitor a second binary question of the pre-determined sequence of binary questions. Finally, the method may include responding to the second binary question of the system with one of: a second affirmative response and a second negative response, where each of the first affirmative response and the second affirmative response causing the system to perform one of: recording and displaying the tilt information; and inflating or deflating the toroidal bladder to the target air pressure, and where each of the first negative response and the second negative response causing the system to return to the test mode.

Yet another embodiment of the disclosure may provide a system for clinical assessment of balance. The system may include a balance platform that is supported under its center by a ball joint, where the ball joint is disposed atop a vertical support that is disposed on a base. The balance platform may include: an upper platform, a lower platform, and a load cell sandwiched between the upper platform and the lower platform. The system may also include a toroidal bladder that supports the lower platform under its periphery, encircles the vertical support, and is disposed on the base. The system may further include an air pressure sensor and a control valve connected to the toroidal bladder. The system may yet further include an inclinometer that is disposed on an underside of the balance platform and measures tilt information of the balance platform in real time. The system may yet further include a computer that: receives, prior to a clinical test, a sensed load from the load cell and proportionately changes a target air pressure of the toroidal bladder for the clinical test, based on the sensed load, to provide a comparable degree of stability across subjects of varying weights, receives a sensed air pressure of the toroidal bladder from the air pressure sensor and sends one of: a first control signal to the control valve to inflate the toroidal bladder when the sensed air pressure is less than the target air pressure provided by the clinical test, and a second control signal to the control valve to deflate the toroidal bladder when the sensed air pressure is greater than the target air pressure provided by the clinical test; and receives the tilt information from the inclinometer. Finally, the system may include a monitor that displays the tilt information in real time.

Yet another embodiment of the disclosure may provide a system for clinical assessment of balance. The system may include a balance platform supported under its center by a ball joint, where the ball joint is disposed atop a vertical support that is disposed on a base. The balance platform may include: an upper platform, a lower platform, and an array of force transducers sandwiched between the upper platform and the lower platform. The system may also include a toroidal bladder that supports the lower platform under its periphery, encircles the vertical support, and is disposed on the base. The system may further include an air pressure sensor and a control valve connected to the toroidal bladder. The system may yet further include an inclinometer that is disposed on an underside of the balance platform and measures tilt information of the balance platform in real time. The system may yet further include a computer that upon selection of a clinical test, receives a control signal to activate one of: the array of force transducers and the inclinometer. If the array of force transducers is activated, then a clinical test is performed to measure changes to a subject's Center of Pressure (CoP) on a stabilized balance platform, and if the inclinometer is activated, then another clinical test is performed to measure the tilt information caused by a subject's movements on a de-stabilized balance platform. Finally, the system may include a monitor that displays the changes to the subject's CoP on the stabilized platform, if the array of force transducers is activated, and the tilt information, if the inclinometer is activated.

BRIEF DESCRIPTION OF THE DRAWINGS

The embodiments herein will be better understood from the following detailed descriptions with reference to the drawings, which are not necessarily drawn to scale and in which.

DETAILED DESCRIPTION

Figure 1A:
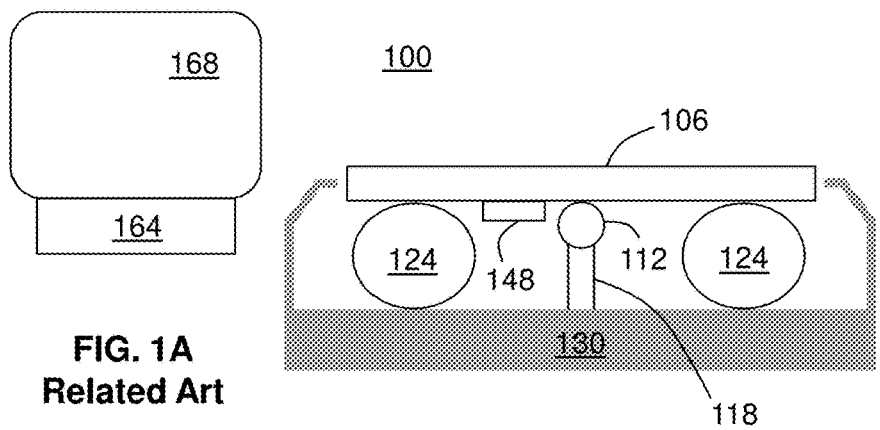
FIG. 1A is a cross section of a schematic diagram illustrating the structure of a system for clinical assessment of balance, in the related art.

The various embodiments of the invention and their various features and details are explained more fully with reference to the non-limiting examples that are illustrated in the accompanying drawings and detailed in the following description. It should be noted that the features and details illustrated in the drawings are not necessarily drawn to scale. Descriptions of well-known materials, components, and processing techniques are omitted so as to not unnecessarily obscure the exemplary systems and methods of the embodiments of the invention. The examples described, below, are intended to facilitate an understanding of ways in which the exemplary systems and methods of the embodiments of the invention may be practiced and to further enable those of skill in the art to practice these exemplary systems and methods. Accordingly, the examples should not be construed as limiting the scope of the exemplary systems and methods of the embodiments of the invention.

Figure 1B:
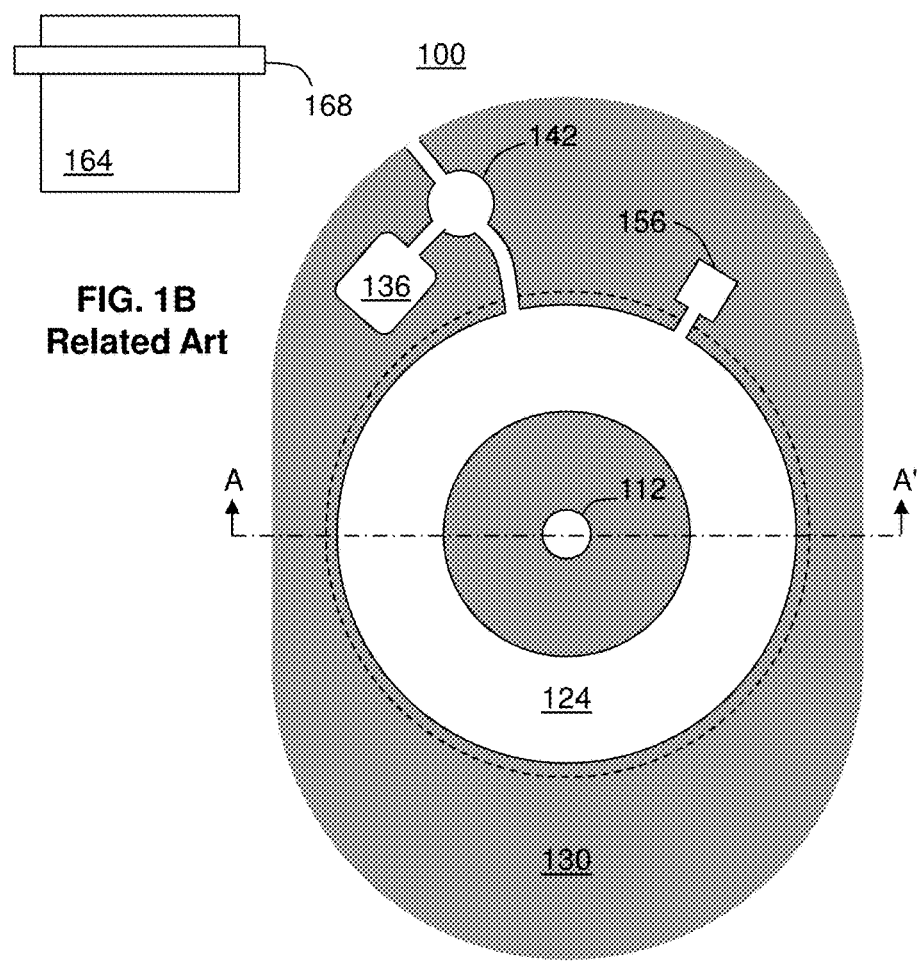
FIG. 1B is a top view of a schematic diagram illustrating the structure of a system for clinical assessment of balance, in the related art.

Using the conventional system 100 illustrated in FIGS. 1A and 1B, the clinical assessment of balance typically includes both inflating and deflating the toroidal bladder 124. During each clinical assessment, a clinician enters one or more air pressures into the computer 164 to control a desired degree of stability for the balance platform 106. While deflating the toroidal bladder 124 from a high pressure to a low pressure can take several seconds or tens of seconds, inflating the toroidal bladder 124 by the air pump 136 from an air pressure of zero to a maximum air pressure of, for example, 15 pounds per square inch (psi), can take more than a minute. This long inflation time unnecessarily prolongs testing for both the subject and the clinician.

Figure 2A:
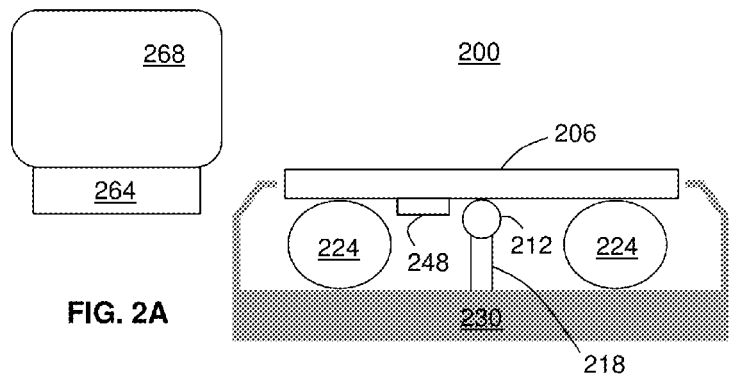
FIG. 2A is a cross section of a schematic diagram illustrating the structure of a system including a high-pressure reservoir for clinical assessment of balance, in embodiments herein.
Figure 2B:
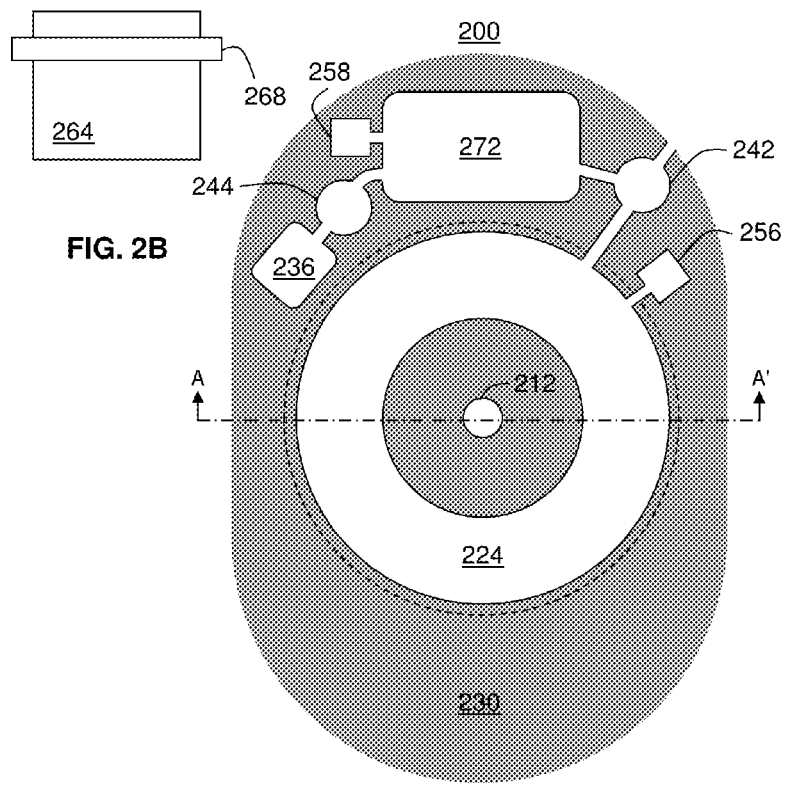
FIG. 2B is a top view of a schematic diagram illustrating the structure of a system including a high-pressure reservoir for clinical assessment of balance, in embodiments herein.

Referring to the system for the clinical assessment of balance 200, illustrated by FIGS. 2A and 2B, an exemplary embodiment of the invention may include a high-pressure reservoir 272 for quickly inflating a toroidal bladder 224 from a low to a high air pressure. The high-pressure reservoir 272 maintains a range of high air pressures that exceed the maximum air pressure for the toroidal bladder 224. The maximum air pressure for the toroidal bladder is pre-determined and related to the lifetime of the bladder, the occurrence of air leaks, and safety. For example, when the maximum air pressure for the toroidal bladder 224 is 15 psi, the high-pressure reservoir 272 may maintain a range of high air pressures between a lowest value of 30 psi and a highest value of 50 psi.

A real time pressure transducer 258 may measure and communicate the pressure of the high-pressure reservoir 272 to a computer 264. Without input from the clinician, the computer 264 may automatically send a control signal to activate air pump 236 and open input valve 244, when the measured pressure of the high-pressure reservoir 272 is less than the exemplary lowest value of 30 psi, allowing air to be pumped into the high-pressure reservoir 272. The air pump 236 continues to pump air into the high-pressure reservoir 272 until the exemplary highest value of 50 psi is reached, at which point, the computer 264 automatically sends another control signal to close the input valve 244 and shut off the air pump 236.

For safety, the lowest and highest values of the range of high air pressures maintained by the high-pressure reservoir 272 are set during manufacture. Although FIG. 2B shows the high-pressure reservoir 272, the real time pressure transducer 258, the input valve 244, and the air pump 236 located within the base 230, any of these structures may alternatively be located outside the base 230.

As instructed by the computer 264, the pressure transducer 258 automatically measures the pressure of the high-pressure reservoir 272 in real time at, for example, 3 Hz to 30 Hz. Preferably, the pressure transducer 258 automatically measures the pressure of the high-pressure reservoir 272 at 20 Hz.

Preferably, pressure transducer 258 wirelessly communicates real time pressure measurements of the high-pressure reservoir 272 to the computer 264, while the computer 264 wirelessly communicates real time control signals to the air pump 236 and the input valve 244 to maintain the range of high air pressures in the high-pressure reservoir 272. Alternatively, the pressure transducer 258, the air pump 236, and the input valve 244 may communicate with the computer 264 via wires.

In an exemplary embodiment of the invention illustrated in the cross section of FIG. 2A, which corresponds to the centerline A-A' of FIG. 2B, and in the top view of FIG. 2B, where the balance platform 206 is removed for illustrative purposes, a ball joint 212, supporting the balance platform 206, may be disposed on a vertical support 218 underneath the center of the balance platform 206. The vertical support 218 and a toroidal bladder 224, made of an elastic material that can be inflated and deflated, may be disposed on a base 230. The toroidal bladder 224 encircles the vertical support 218 and supports the periphery of the undersurface of the balance platform 206. Under control of the computer 264, the toroidal bladder 224 may be inflated by the high-pressure reservoir 272 through a control valve 242 to restrain downward tilting of the balance platform 206 and provide greater stability to the balance platform 206; while deflation of the toroidal bladder 224 through the control valve 242 to the atmosphere facilitates downward tilting of the balance platform 206 and provides lesser stability to the balance platform 206.

As instructed by the computer 264, the air pressure sensor 256 may automatically measure an air pressure of the toroidal bladder 224 in real time at, for example, 3 Hz to 30 Hz. Preferably, the air pressure sensor 256 automatically measures the air pressure of the toroidal bladder 224 at 20 Hz.

Preferably, air pressure sensor 256 wirelessly communicates real time air pressure measurements of the toroidal bladder 224 to the computer 264, while the computer 264 wirelessly communicates real time control signals to the control valve 242 for inflating and deflating the toroidal bladder 224 to a target air pressure input from the computer 264 and corresponding to one or more stages of a clinical test for the assessment of balance. To rapidly inflate the toroidal bladder 224 to the target air pressure, the computer 264 wirelessly sends a control signal to open the control valve 242 between the high-pressure reservoir 272 and the toroidal bladder 224 and wirelessly sends another control signal to close the control valve 242, when the air pressure sensor 256 measures the air pressure within the toroidal bladder 224 as equal to the target air pressure. In the case of wireless communication, the computer 264 may send a set point to the control valve 242, which may be controlled by a local controller (not shown), in order to prevent inflation or deflation during periods when wireless communication is lost. Similarly, to deflate the toroidal bladder 224 to the target air pressure, the computer 264 wirelessly sends a control signal to open the control valve 242 between the high-pressure reservoir 272 and the atmosphere and wirelessly sends another control signal to close the control valve 242, when the air pressure sensor 256 measures the air pressure within the toroidal bladder 224 as equal to the target air pressure. Alternatively, the air pressure sensor 256 and the control valve 242 may communicate with the computer 264 via wires.

An inclinometer 248, e.g., an electronic dual-axis accelerometer, may be disposed on the underside of the balance platform 206, to measure the direction of tilt of the balance platform 206 in the horizontal x-y plane when supported by the ball joint 212 and the degree of tilt of the balance platform 206 relative to the vertical z-axis in response to the subject's real time movements at a rate of, for example, 5 to 200 Hz. Preferably, the inclinometer 248 measures the direction of tilt and the degree of tilt of the balance platform 206 at a rate of 50 Hz and sends this tilt information to the computer 264. The computer 264 may display this tilt information on a monitor 268 in real time, and store the tilt information in the subject's computer files. The computer 264 may also calculate a rate of change of the degree of tilt of the balance platform 206 along the z-axis by subtracting a previously received degree of tilt from a currently received degree of tilt, display the calculated rate of change of the degree of tilt on the monitor 268, and store the calculated rate of change of the degree of tilt in the subject's computer files.

Preferably, the inclinometer 248 wirelessly communicates real time measurements of the direction of tilt, the degree of tilt, and the calculated rate of change of the degree of tilt of the balance platform 206 to the computer 264. Alternatively, the inclinometer 248 communicates with the computer 264 via wires.

While conducting a clinical test, safety requires that the subject mount a stable balance platform 206. Following entry of a test mode on the computer 264 of the system 200, an exemplary embodiment of the invention may rapidly and automatically inflate the toroidal bladder 224 to a maximum air pressure of, for example, 15 psi, by automatically activating the control valve 242 to allow high-pressure air to quickly flow from the high-pressure reservoir 272 to the toroidal bladder 224. When the air pressure sensor 256 senses an air pressure of the toroidal bladder 224 equal to the maximum air pressure, the control valve 242 is automatically turned off and the subject may safely mount the stabilized balance platform 206.

Conventionally, before conducing a clinical test, the clinician was required to enter a number of test criteria, e.g., both feet together or apart, only right foot or only left foot, hands on or off a safety bar, eyes open or closed, duration of each stage of the test, and a target air pressure of the toroidal bladder for one or more stages of the clinical test. In an exemplary embodiment of the invention, however, the clinician may select a particular clinical test and may subsequently respond to a pre-determined sequence of binary questions that are automatically displayed in a large font, so as to be easily read at a distance of several feet, by a computer monitor of a system for the clinical assessment of balance. The display of each of the pre-determined sequence of binary questions may be accompanied by an auditory cue.

Figure 3:
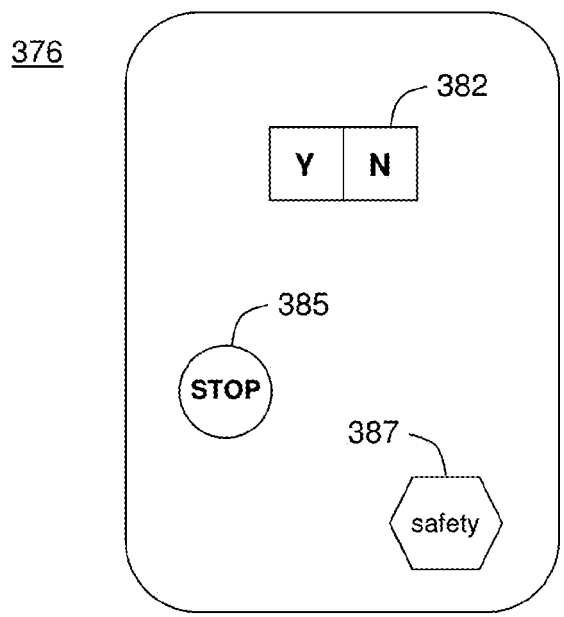
FIG. 3 is a top view of a schematic diagram illustrating a structure of a hand-held device used with a system for clinical assessment of balance, in embodiments herein.

Referring to FIG. 3, the response to each of the pre-determined sequence of binary questions may be entered via a hand-held input device 376, allowing the clinician to more easily focus his or her attention on the subject during each stage of the clinical test, rather than attending to keyboard or touch-screen response inputs to the computer of the system. The pre-determined sequence of binary questions is based on extensive clinical experience over a large population of subjects for each clinical test. The response of the clinician to each of the binary questions may result in automatically recording, displaying and/or calculating the tilt information of the selected clinical test, automatically inflating/deflating the toroidal bladder to a target air pressure for the selected clinical test, and automatically saving the tilt information of the selected clinical test to computer files, as described below.

Alternatively, a pre-determined sequence of binary questions may be provided to the clinician by computer-implemented text to speech functionality, and/or spoken responses to the pre-determined sequence of binary questions from the clinician may be provided to the computer by speech recognition software. The clinician may wear a wireless headset to hear the computer-spoken pre-determined sequence of binary questions and/or to respond to the pre-determined sequence of binary questions by voice commands.

The hand-held input device 376 may have a few simple input switches, each of which the clinician easily activates by touch, sensing any of size, shape, location, or texture of the input switches, without necessarily looking at the hand-held input device 376. The hand-held input device 376 may include a binary input 382, e.g., a toggle switch, a selector switch, a rocker switch, a pair of pushbutton switches, etc., that allows the clinician to respond to each of the pre-determined sequence of binary questions associated with each selected clinical test. The hand-held input device 376 may also include a separate stop input 385, e.g., a button or toggle switch, allowing the clinician to stop the recording of the selected clinical test data at any stage of testing. The hand-held input device 376 may also include a separate safety input 387, e.g., a button or toggle switch, that causes the toroidal bladder to inflate to its pre-determined maximum air pressure, so the subject may safely dismount the now stabilized balance platform.

Preferably, the hand-held input device 376 is battery powered and wirelessly communicates the clinician's response to each binary question displayed by the computer monitor when the clinician activates the binary input 382. Similarly, the stop input 385 and safety input 387 may also wirelessly communicate with the computer. Alternatively, the hand-held input device 376 including the binary input 382, the stop input 385, and the safety input 387 may be electrically powered by wires and may communicate with the computer via wires.

An exemplary embodiment of the invention may allow the clinician to select, from the test mode on the computer of the system, a modified Clinical Test of Sensory Interaction on Balance (mCTSIB) that initially performs two 30 second static balance tests, with eyes open and eyes closed, on a stable balance platform and subsequently performs two 30 second static balance tests, with eyes open and eyes closed, on a balance platform with a controlled degree of stability. Each of the two 30 second static balance tests is performed with hands off the safety bar and both feet together.

Figure 4:
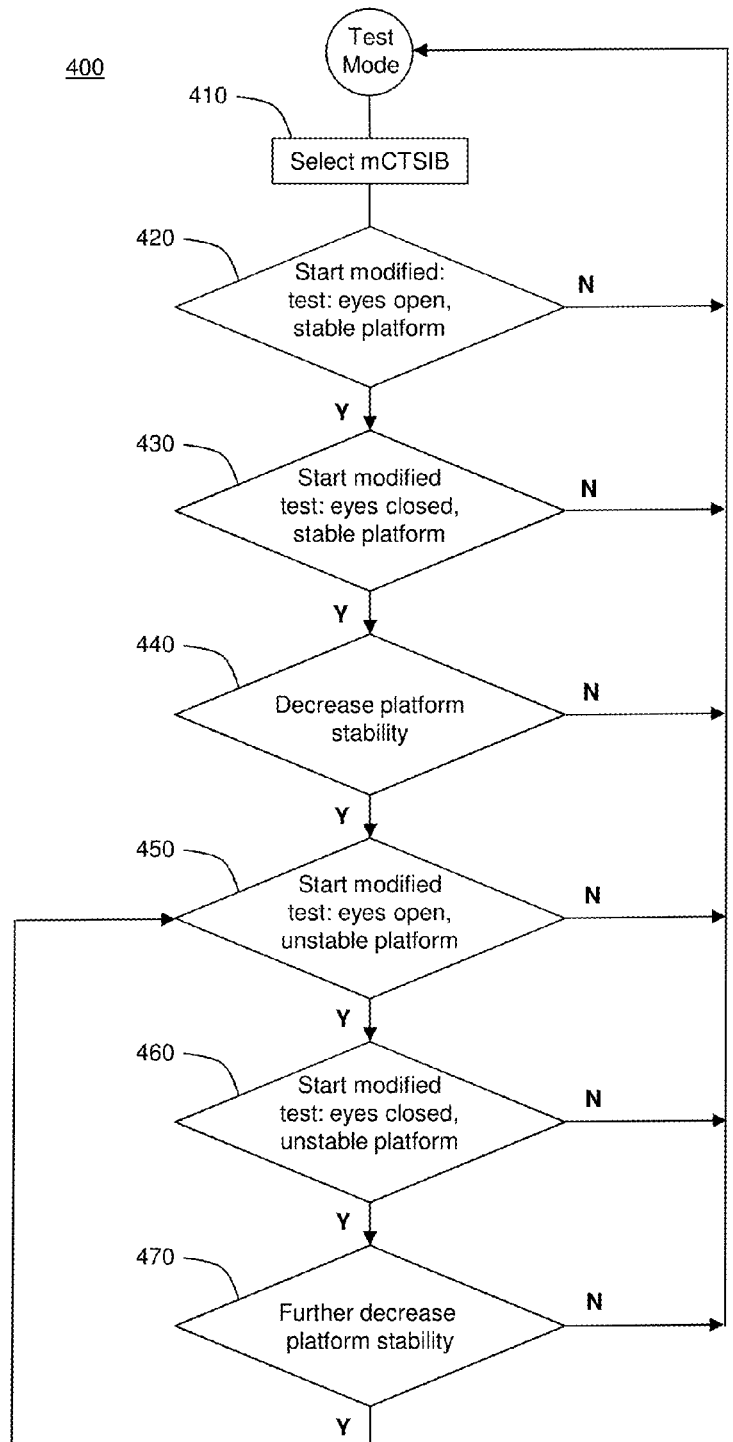
FIG. 4 is a flow chart of a method of performing a modified Clinical Test of Sensory Interaction on Balance (mCTSIB), using a pre-determined sequence of binary questions, for clinical assessment of balance, in embodiments herein.

Referring to FIG. 4, an exemplary method 400 allows the clinician to select the mCTSIB from the test mode of the system, using keyboard or touch-screen inputs to the computer in step 410. Following entry into the test mode, the toroidal bladder may be automatically inflated to its maximum target air pressure, e.g., 15 psi, and the subject may safely mount the stabilized balance platform. Under control of the computer, the toroidal bladder may be inflated by one of: an air pressure pump, as shown in FIG. 1B, and a high-pressure reservoir, as shown in FIG. 2B, through a control valve corresponding to one of elements: 142 of FIG. 1B and 242 of FIG. 2B, respectively, to restrain downward tilting of the balance platform and provide greater stability to the balance platform. Similarly, deflation of the toroidal bladder under control of the computer, through the control valve by venting to the atmosphere, facilitates downward tilting of the balance platform, providing lesser stability to the balance platform.

Following selection of the mCTSIB, the computer activates the inclinometer and the monitor clearly displays a first pre-determined binary question, for example, "Start modified test: eyes-open, stable platform—Y/N?" in step 420. The clinician initiates the first test with eyes open on a stable balance platform by providing an affirmative binary input, "Y", with the hand-held input device 376 or keyboard or touch-screen inputs to the computer. The computer then automatically displays on the monitor and records, for 30 seconds, the tilt information including the detected direction of tilt in the x-y plane, the degree of tilt along the z-axis, and the calculated rate of change of the degree of tilt along the z-axis for the first test of the initial two 30 second static balance tests. In an exemplary embodiment of the invention, a "near fall" or loss of balance, during any stage of the mCTSIB, may be indicated in the display and recorded by the computer when the rate of change of the degree of tilt along the z-axis is greater than or equal to, for example, +/−8 degrees per second. If the clinician provides a negative binary input, "N", to the first pre-determined binary question, then the system returns to the test mode.

After displaying and recording the tilt information of the first test with eyes open on the stabilized platform for the mCTSIB, the monitor clearly displays a second pre-determined binary question, for example, "Start modified test: eyes-closed, stable platform—Y/N?" in step 430. The clinician initiates the second test with eyes closed on the stable balance platform by providing an affirmative binary input, "Y", to the computer. The computer then automatically displays on the monitor and records, for 30 seconds, the tilt information for the second test with eyes closed on the stabilized platform for the mCTSIB. Again, a "near fall" or loss of balance, during any stage of the mCTSIB, may be indicated in the display and recorded, when the rate of change of the degree of tilt along the z-axis is greater than or equal to, for example, +/−8 degrees per second. If the clinician provides a negative binary input, "N", to the second pre-determined binary question, then the system returns to the test mode.

After displaying and recording the tilt information of the initial two 30 second static balance tests of the mCTSIB on the stabilized platform with eyes open and closed, the monitor clearly displays a third pre-determined binary question, for example, "Decrease platform stability—Y/N?" in step 440. As the balance platform was stabilized at its maximum target air pressure, e.g., 15 psi, for the first two 30 second static balance tests of the mCTSIB, the air pressure of the toroidal bladder must be deceased before conducting the second two 30 second static balance tests of the CTSIB on an unstable balance platform. The clinician decreases the stability of the balance platform by providing an affirmative binary input, "Y", to the third pre-determined binary question. Upon entering an affirmative input, air pressure in the toroidal bladder is decreased by venting its air to the atmosphere through a control valve under control of the computer.

Extensive clinical experience indicates that a target air pressure of, for example, 8 psi, provides a good clinical assessment of balance for many subjects on an unstable balance platform in the mCTSIB. While the balance platform decreases to a degree of stability corresponding to the target air pressure of an exemplary 8 psi for the supporting toroidal bladder, the clinician may instruct the subject to hold on to a safety bar; alternatively, the clinician may physically support the subject. If the clinician provides a negative binary input, "N", to the third pre-determined binary question, then the system returns to the test mode.

After the balance platform's degree of stability is decreased, the monitor clearly displays a fourth pre-determined binary question, for example, "Start modified test: eyes open, unstable platform—Y/N?" in step 450. The clinician initiates the first test with eyes open on an unstable balance platform by providing an affirmative binary input, "Y", to the computer. The computer then automatically displays on the monitor and records, for 30 seconds, the tilt information for the first test with eyes open on the unstable balance platform. Again, a "near fall" or loss of balance, during any stage of the mCTSIB, may be indicated in the display and recorded, when the rate of change of the degree of tilt along the z-axis is greater than or equal to, for example, +/−8 degrees per second. If the clinician provides a negative binary input, "N", to the fourth pre-determined binary question, then the system returns to the test mode.

After displaying and recording the tilt information of the first of the two 30 second static balance tests on the unstable platform, the monitor clearly displays a fifth pre-determined binary question, for example, "Start modified test: eyes-closed, unstable platform—Y/N?" in step 460. The clinician initiates the second static balance test with eyes closed on the unstable balance platform by providing an affirmative binary input, "Y", to the computer. The computer then automatically displays on the monitor and records, for 30 seconds, the tilt information for the second of the two 30 second static balance tests with eyes closed on the unstable platform. Again, a "near fall" or loss of balance, during any stage of the mCTSIB, may be indicated in the display and recorded when the rate of change of the degree of tilt along the z-axis is greater than or equal to, for example, +/−8 degrees per second. If the clinician provides a negative binary input, "N", to the fifth pre-determined binary question, then the system returns to the test mode.

After displaying and recording the tilt information of the two 30 second static balance tests of the mCTSIB on the unstable balance platform, it may be the case that the subject has maintained his or her balance on the unstable balance platform, i.e., has not suffered a "near fall" or a loss of balance. Hence, after displaying and recording the tilt information of the two 30 second static balance tests on the unstable platform, the monitor may clearly display a sixth pre-determined binary question, for example, "Further decrease platform stability—Y/N?" in step 470.

As the toroidal bladder supporting the balance platform previously had a target air pressure of 8 psi, for the two 30 second static balance tests on the unstable platform, the target air pressure of the toroidal bladder may now further automatically decease by, for example, a difference of −2 psi, to yield a target air pressure equal to 6 psi before conducting another two 30 second static balance tests of the CTSIB on a further de-stabilized balance platform. The clinician further decreases the degree of stability of the unstable balance platform by providing an affirmative binary input, "Y", to the sixth pre-determined binary question, which causes the toroidal bladder to further deflate and the system to return to step 450, i.e., "Start modified test: eyes open, unstable platform—Y/N?" In this manner, the clinician may further sequentially conduct two 30 second static balance tests with eyes open and eyes closed on a sequentially further de-stabilized unstable balance platform, until a "near fall" or a loss of balance is displayed on the monitor and recorded by the computer for the mCTSIB. If the clinician provides a negative binary input, "N", to the sixth pre-determined binary question, then the system returns to the test mode.

Another exemplary embodiment of the invention may allow the clinician to select modified Limits of Stability (mLOS) tests that require a subject to stretch, by leaning his or her upper body with extension of an upper limb, as far as possible in three directions—forward, left, and right—without losing his or her balance, or changing his or her stance upon an unstable balance platform with hands off the safety bar, eyes open, and feet apart. The subject's loss of balance in any direction may be indicated when the rate of change of the degree of tilt along the z-axis is greater than or equal to, for example, +/−8 degrees per second.

Figure 5:
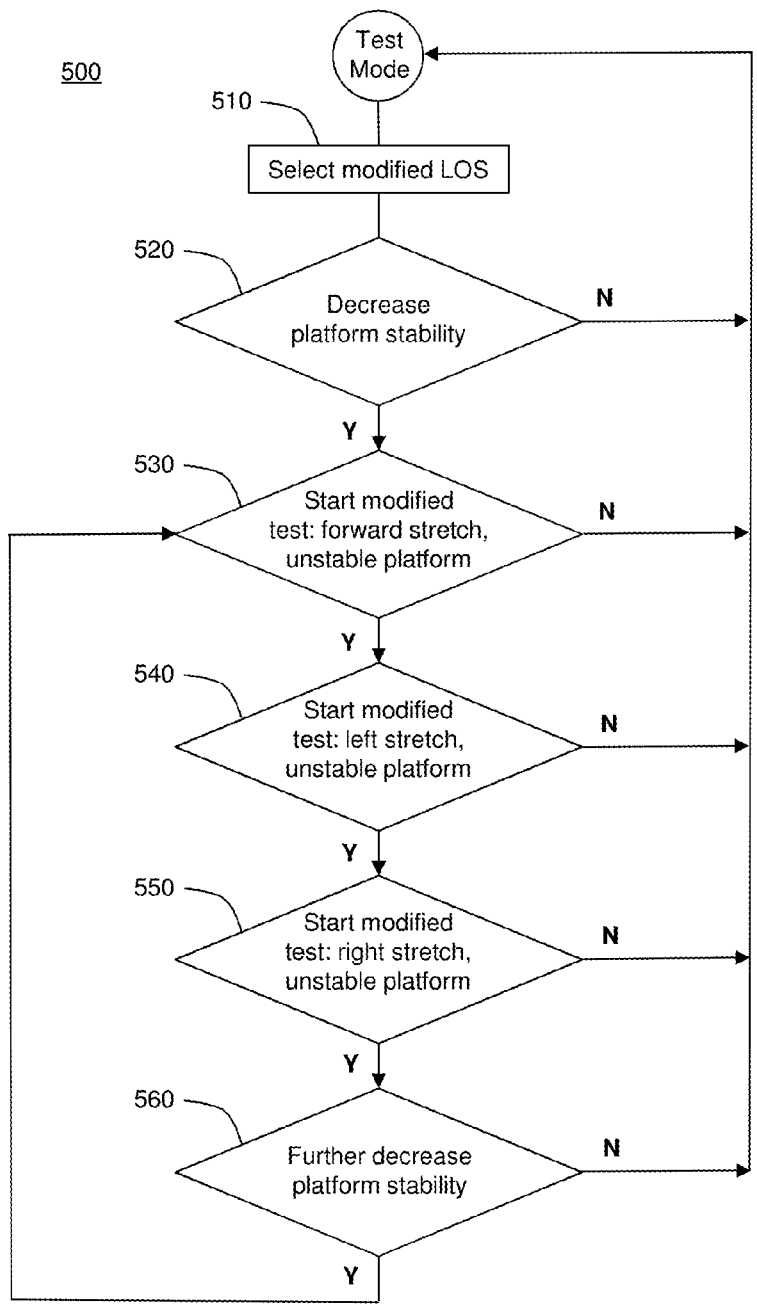
FIG. 5 is a flow chart of a method of performing modified Loss of Stability (LOS) tests, using a pre-determined sequence of binary questions, for clinical assessment of balance, in embodiments herein.

Referring to FIG. 5, an exemplary method 500 may allow the clinician to select mLOS tests, from the test mode of the system, using keyboard or touch-screen inputs to the computer in step 510. Upon entry into the test mode, the toroidal bladder is inflated to its maximum target air pressure, e.g., 15 psi, and the subject may safely mount the stabilized balance platform. Under control of the computer, the toroidal bladder may be inflated by one of: an air pressure pump, as shown in FIG. 1B, and a high-pressure reservoir, as shown in FIG. 2B, through a control valve corresponding to one of elements: 142 of FIG. 1B and 242 of FIG. 2B, respectively, to restrain downward tilting of the balance platform and provide greater stability to the balance platform. Similarly, deflation of the toroidal bladder under control of the computer, through the control valve by venting to the atmosphere, facilitates downward tilting of the balance platform, providing lesser stability to the balance platform.

Following selection of the mLOS tests, the computer activates the inclinometer and the monitor clearly displays a first pre-determined binary question, for example, "Decrease platform stability—Y/N?" in step 520. The clinician decreases the stability of the balance platform by providing an affirmative binary input, "Y", to the first pre-determined binary question with the hand-held input device 376 or keyboard or touch-screen inputs to the computer. Upon entering an affirmative input, air pressure in the toroidal bladder is decreased by venting its air to the atmosphere under control of the computer. Extensive clinical experience indicates that a target air pressure of, for example, 8 psi, provides an air pressure, where many subjects performing the mLOS tests will lose their balance. While the balance platform decreases to a degree of stability corresponding to the target air pressure of the exemplary 8 psi for the supporting toroidal bladder, the clinician may instruct the subject to hold on to a safety bar; alternatively, the clinician may physically support the subject. If the clinician provides a negative binary input, "N", to the first pre-determined binary question, then the system returns to the test mode.

After the degree of the balance platform's stability is decreased, the monitor clearly displays a second pre-determined binary question, for example, "Start modified test: forward stretch, unstable platform—Y/N?" in step 530. The clinician initiates a first forward stretch mLOS test on an unstable balance platform by providing an affirmative binary input, "Y", to the computer. The computer then automatically displays on the monitor and records, for about 10 seconds, the tilt information including the detected direction of tilt in the x-y plane, the degree of tilt along the z-axis, and the calculated rate of change of the degree of tilt along the z-axis for the first forward stretch mLOS test on the unstable balance platform. Again, a "near fall" or loss of balance, during any stage of the mLOS, may be indicated in the display and recorded, when the rate of change of the degree of tilt along the z-axis is greater than or equal to, for example, +/−8 degrees per second. If the clinician provides a negative binary input, "N", to the second pre-determined binary question, then the system returns to the test mode.

After displaying and recording the tilt information of the first forward stretch mLOS test on the unstable platform, the monitor clearly displays a third pre-determined binary question, for example, "Start modified test: left stretch, unstable platform—Y/N?" in step 540. The clinician may initiate the first left stretch mLOS test on the unstable balance platform by providing an affirmative binary input, "Y", to the computer. The computer then automatically displays on the monitor and records, for about 10 seconds, the tilt information including the detected direction of tilt in the x-y plane, the degree of tilt along the z-axis, and the calculated rate of change of the degree of tilt along the z-axis for the first left stretch mLOS test on the unstable platform. Again, a "near fall" or loss of balance, during any stage of the mLOS, may be indicated in the display and recorded when the rate of change of the degree of tilt along the z-axis is greater than or equal to, for example, +/−8 degrees per second. If the clinician provides a negative binary input, "N", to the third pre-determined binary question, then the system returns to the test mode.

After displaying and recording the tilt information of the first left stretch mLOS test on the unstable balance platform, the monitor clearly displays a fourth pre-determined binary question, for example, "Start modified test: right stretch, unstable platform—Y/N?" in step 550. The clinician may initiate the first right stretch mLOS test on the unstable balance platform by providing an affirmative binary input, "Y", to the computer. The computer then automatically displays on the monitor and records, for about 10 seconds, the tilt information including the detected direction of tilt in the x-y plane, the degree of tilt along the z-axis, and the calculated rate of change of the degree of tilt along the z-axis for the first right stretch mLOS test on the unstable balance platform. Again, a "near fall" or loss of balance, during any stage of the mLOS, may be indicated in the display and recorded when the rate of change of the degree of tilt along the z-axis is greater than or equal to, for example, +/−8 degrees per second. If the clinician provides a negative binary input, "N", to the fourth pre-determined binary question, then the system returns to the test mode.

After displaying and recording the tilt information of the first forward, left, and right stretch MLOS tests on the unstable balance platform supported by a toroidal bladder inflated to an exemplary target air pressure of 8 psi, it may be the case that the subject has maintained his or her balance on the unstable balance platform, i.e., has not undergone a "near fall" or a loss of balance. Hence, after displaying and recording the tilt information of the three directional mLOS tests on the unstable balance platform, the monitor may clearly display a fifth pre-determined binary question, for example, "Further decrease platform stability—Y/N?" in step 560.

As the balance platform was stabilized at the exemplary target air pressure of 8 psi, for the first forward, left, and right stretch mLOS tests on the unstable balance platform, the target air pressure of the toroidal bladder may further decease by, for example, a difference of −2 psi, to yield a target air pressure equal to 6 psi before conducting another three directional mLOS tests on the further de-stabilized balance platform. The clinician further decreases the degree of stability of the unstable balance platform by providing an affirmative binary input, "Y", to the fifth pre-determined binary question, which causes the toroidal bladder to further deflate and the system to return to step 530, i.e., "Start modified test: forward stretch, unstable platform—Y/N?" In this manner, the clinician may sequentially conduct additional forward, left, and right stretch MLOS tests on a sequentially further de-stabilized balance platform, until a "near fall" or a loss of balance is displayed and recorded. If the clinician provides a negative binary input, "N", to the fifth pre-determined binary question, then the system returns to the test mode and the three initial mLOS tests are complete.

In a conventional force measurement system for assessing balance, a subject's movements upon a horizontal stable force plate result in changes to the center of pressure (CoP), as measured by multiple force transducers or load cells positioned underneath the force plate. A computer converts the outputs of the multiple force transducers into vector components, including a left/right force component, $F_x$, and a forward/backward force component, $F_y$. A vertical force component, $F_z$, which depends on the subject's weight, may be determined by summing all the vertical force components from all of the multiple force transducers. The CoP is computed using these vector components and the subject's height, which often serves as a proxy for the height of the subject's center of gravity above the force plate. Differences in the subject's computed CoPs are used to calculate the subject's angle of sway in real time.

In contrast, the degree of tilt along the z-axis of an exemplary embodiment of the invention depends not only on the subject's movements upon the balance platform, but also on the value of the air pressure that inflates the toroidal bladder supporting the balance platform, i.e., the degree of the balance platform's stability. The toroidal bladder may be viewed as a compression spring, whose degree of compression along the z-axis depends on the subject's weight. Thus, for a particular movement, for example, a maximal stretch to the left, a subject, who weighs more, will compress the toroidal bladder more, giving a greater degree of tilt along the z-axis.

To more readily assess the tilt information, including the detected direction of tilt in the x-y plane, the degree of tilt along the z-axis, and the calculated rate of change of the degree of tilt along the z-axis, across subjects of varying weights for a clinical test, it may be beneficial to proportionately increase the inflation pressure of the toroidal bladder for a subject who weighs more, relative to a subject who weighs less, so as to provide a comparable degree of a balance platform's stability across subjects of varying weights in an exemplary embodiment of the invention.

Figure 6:
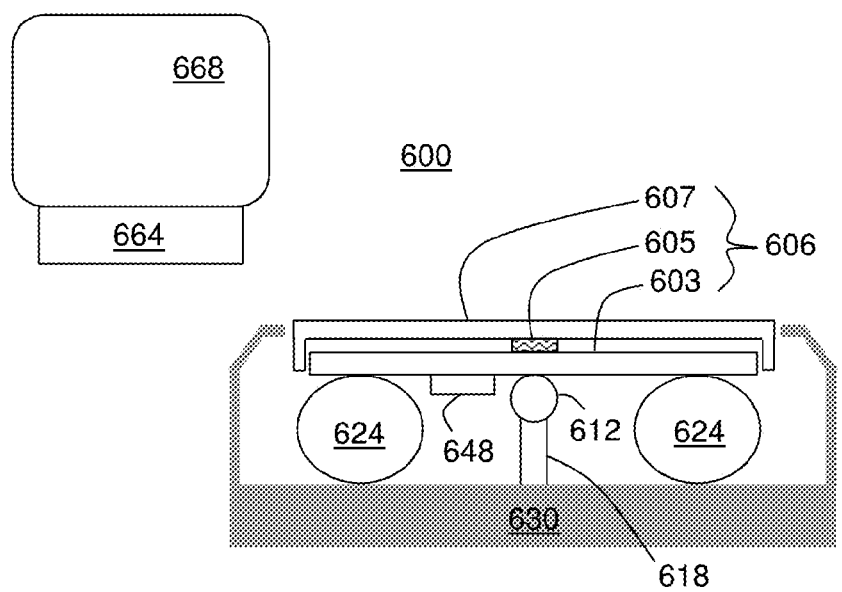
FIG. 6 is a cross section of a schematic diagram illustrating the structure of a system including a load cell for clinical assessment of balance, in embodiments herein.

As illustrated in FIG. 6, an exemplary embodiment of a system 600 that provides a comparable degree of a balance platform's stability for subjects of different weights may include a balance platform 606 further including: an upper platform 607 upon which the subject stands; a load cell 605 that measures a load, which depends upon the subject's weight; and a lower platform 603 that supports the load cell 605. The load cell 605 may be sandwiched between and disposed near the centers of the upper platform 607 and the lower platform 603. In turn, the lower platform 603 may be supported by a ball joint 612 that is disposed on a vertical support 618 underneath the center of the lower platform 603 of the balance platform 606. The vertical support 618 and a toroidal bladder 624, made of an elastic material, may be disposed on a base 630. The toroidal bladder 624 may encircle the vertical support 618 and support the lower platform 603 of the balance platform 606 under its periphery. With the exception of the load cell 605, the structural elements of system 600 function like those structural elements of systems 100 and 200.

Under control of the computer 664, the toroidal bladder 624 may be inflated by one of: an air pressure pump, as shown in FIG. 1B, and a high-pressure reservoir, as shown in FIG. 2B, through a control valve corresponding to one of elements: 142 of FIG. 1B and 242 of FIG. 2B, respectively, to restrain downward tilting of the balance platform 606 and provide greater stability to the balance platform 606. Similarly, deflation of the toroidal bladder 624 under control of the computer 664, through the control valve by venting to the atmosphere, facilitates downward tilting of the lower platform 603 of the balance platform 606, providing lesser stability to the balance platform 606.

For example, in two parallel mCTSIB clinical tests for two subjects, a degree of the balance platform's stability, e.g., that of a "stable" platform, may be provided by a toroidal bladder 624 inflated to a first target air pressure of, for example, 12 psi, for a first subject weighing 140 lbs, whereas a comparable degree of the balance platform's stability may be provided by the toroidal bladder 624 being inflated to a second target air pressure of, for example, 15 psi, for a second subject weighing 225 lbs. Similarly, an unstable balance platform 606 with a first target air pressure of 8 psi may be provided for the first subject weighing 140 lbs, whereas an unstable balance platform 606 with a second target air pressure of 11 psi may be provided for the second subject weighing 225 lbs.

An inclinometer 648, e.g., an electronic dual-axis accelerometer, disposed on the underside of the lower platform 603 of the balance platform 606, measures a direction of tilt of the balance platform 606 relative to the supporting ball joint 612 in the horizontal x-y plane and a degree of tilt of the balance platform 606 relative to the z-axis of the supporting ball joint 612, and sends this tilt information to the computer 664. The computer 664 may calculate a rate of change of the degree of tilt along the z-axis. A computer 664, in communication with the inclinometer 548, may receive the detected direction of tilt and the degree of tilt of the balance platform 506 in real time, display this tilt information on a monitor 668 in real time, and store the tilt information in the subject's computer files.

As described above, before conducting a clinical test, safety requires that the subject mount a stable balance platform 606. Upon entering the test mode of the computer 664 of the system 600, an exemplary embodiment of the invention may automatically inflate the toroidal bladder 624 to a maximum target air pressure of, for example, 15 psi. When the air pressure sensor, corresponding to one of elements: 156 of FIG. 1B and 256 of FIG. 2B, senses an air pressure of the toroidal bladder 624 equal to the maximum target air pressure, the computer 664 may automatically transmit an instruction, e.g., "Step on platform for weighing", to the monitor 668 for clear display to the subject and the clinician in a large font, so as to be easily read at a distance of several feet. The displayed instruction may be accompanied by an auditory cue. At the same time, the computer 664 may activate the load sensor 605 for several seconds. The subject may then mount the balance platform 606, and the sensed load is then communicated to the computer 664 from the load cell 605. The load cell 605 may then be de-activated and the inclinometer 648 activated for the following clinical test.

The sensed load of the subject on the stable balance platform 606 is slightly less than the actual weight of the subject, because a fraction of the actual weight of the subject compresses the toroidal bladder 624 and is not sensed by the overlying load cell 605. However, the loads sensed at different values of inflatable air pressures may readily be calibrated to actual weights during manufacture of the system 600 and the results stored in the computer 664. These results may then be used to change the degree of stability of the balance platform 606 for subjects of different weights, by changing the inflation air pressure of the toroidal bladder 624 based on the subject's weight, to more readily allow comparison of tilt information including the direction of tilt in the x-y plane, the degree of tilt along the z-axis, and the calculated rate of change of tilt along the z-axis among clinical tests across subjects of different weights.

Alternatively, in a system that does not include a load sensor or its functional equivalent, e.g., systems 100, 200, to sense a subject's weight on the corresponding balance platforms 106, 206, the clinician may enter the subject's weight into the corresponding computers 164, 264, via the keyboard or the touch-screen before initiating a clinical test. This entered weight may then be used to change the degree of stability of the corresponding balance platforms 106, 206, for subjects of different weights.

Figure 7A:
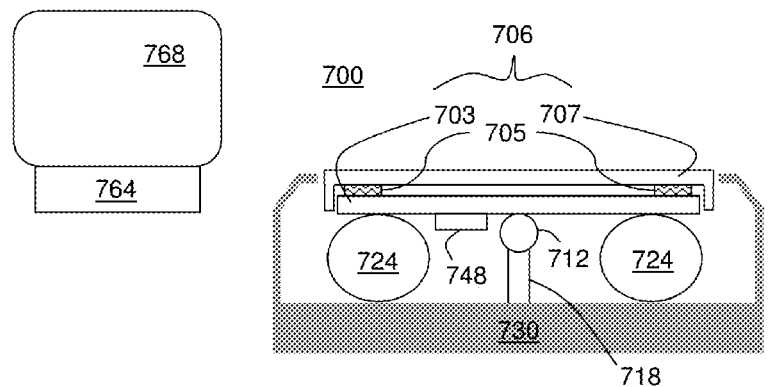
FIG. 7A is a cross section of a schematic diagram illustrating the structure of a system including an activated array of force transducers for measuring changes of Center of Pressure on a stabilized balance platform for clinical assessment of balance, in embodiments herein.
Figure 7B:
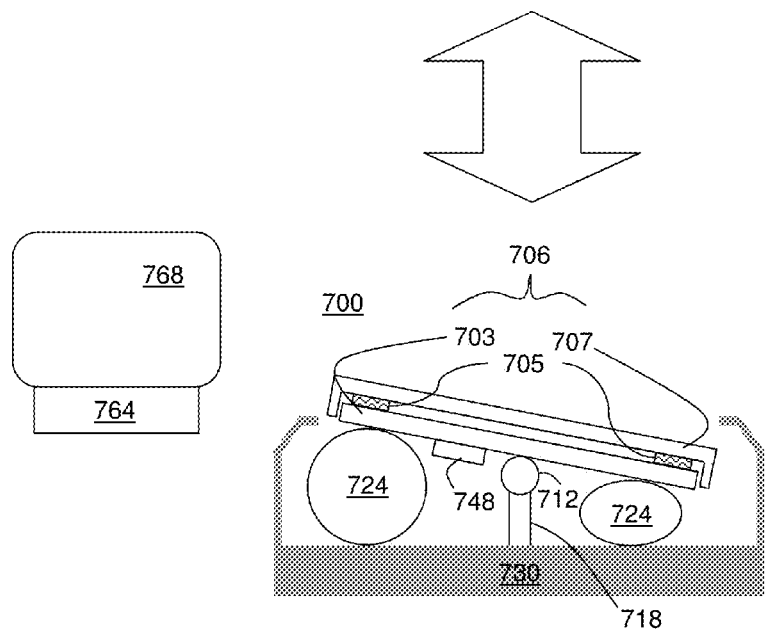
FIG. 7B is a cross section of a schematic diagram illustrating the structure of a system including an activated inclinometer for measuring tilt information on a de-stabilized balance platform for clinical assessment of balance, in embodiments herein.

An exemplary embodiment of a system 700 for clinical assessment of balance may include both: a force measurement system that receives real time force measurements from an array of force transducers attached to a horizontally-stabilized balance platform 706 on which a subject stands, as illustrated in FIG. 7A; and a tilting balance platform system that receives real time tilt measurements, including a direction of tilt in the x-y plane, a degree of tilt along the z-axis, and a calculated rate of change of tilt along the z-axis, from a relatively unstable balance platform 706 on which a subject stands, as illustrated in FIG. 7B. Thus, a clinician may easily conduct clinical tests that call for either force measurements on a horizontally-stabilized balance platform 706 or clinical tilt measurements from a stability-controlled balance platform 706 with but a single system 700.

Referring to the cross section of FIG. 7A, the system 700, as configured for a force measurement system may include a balance platform 706 further including: an upper platform 707 that functions as a force plate on which the subject stands; an array of force transducers 705, attached to upper platform 707, that measure force vector components in the horizontal x-y plane resulting from a subject's movements; and a lower platform 703 that supports the array of force transducers 705. The array of force transducers 705 is sandwiched between the upper platform 707 and the lower platform 703. For example, a quadrilateral array of force transducers may be disposed adjacent to the circumference of the lower platform 703 at positions corresponding to, for example, 0°, 90°, 180°, and 270°. The lower platform 703 is supported by a ball joint 712 that is disposed on a vertical support 718 underneath the center of the lower platform 703. The vertical support 718 and a toroidal bladder 724, made of an elastic material, are disposed on a base 730. The toroidal bladder 724 encircles the vertical support 718 and supports the lower platform 703 along its periphery. The toroidal bladder 724 is inflated by one of: an air pump corresponding to the air pump 136 of FIG. 1B and a high-pressure reservoir corresponding to the high-pressure reservoir 272 of FIG. 2B, respectively, to its maximum target air pressure, so as to restrain downward tilting of the balance platform 706; thus, stabilizing the balance platform 706. With the exception of the array of force transducers 705, the structural elements of system 700 function like those structural elements of systems 100 and 200.

The array of force transducers 705 measures, in real time, changes to the subject's Center of Pressure (CoP) caused by the subject's movements on the stabilized balance platform 706 and communicates the measures to the computer 764 at a rate of, for example, 5 to 200 Hz. Preferably, the array of force transducers 705 measures changes to the subject's CoP at a rate of 50 Hz. A computer 664, connected to the array of force transducers 705, receives the measured changes to the subject's CoP and computes the corresponding changes to force vector components, $F_x$ and $F_y$, caused by the subject's movements on the stabilized balance platform 706, which are then displayed on the monitor 768 and stored by the computer 764. Preferably, the computer 764 wirelessly communicates control signals, e.g., activation and de-activation, to the array of force transducers 705 and wirelessly receives real time measurements of changes to the subject's CoP from the array of force transducers 705. Alternatively, the array of transducers 705 may communicate by wires with the computer 764.

In a conventional force measurement system, the force transducers are supported by rigid structures that contact the floor. In an exemplary embodiment of the system 700, however, the array of force transducers 705 is supported by the lower platform 703, which in turn is supported by the toroidal bladder 724. Typically, at its maximum target air pressure, for example, 15 psi, the toroidal bladder 724 yields little tilt along its z-axis, in response to even relatively large movements by the subject; thus, providing a horizontal stabilized balance platform 706 for force measurements.

Figure 8:
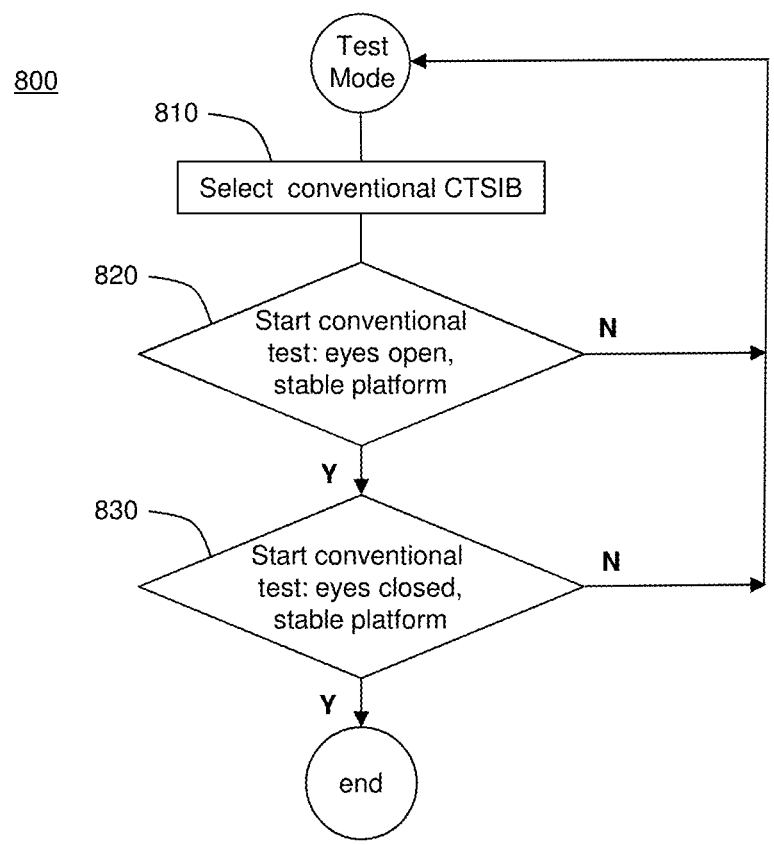
FIG. 8 is a flow chart of a method of performing a conventional CTSIB, using the structure of FIG. 7A, for clinical assessment of balance, in embodiments herein.

Referring to FIG. 8, an exemplary method 800 of using the system 700 for force plate measurements may allow the clinician to select a conventional Clinical Test of Sensory Interaction on Balance (CTSIB) that measures, by the array of force transducers 705, changes to the subject's CoP caused by the subject's movements on a stabilized balance platform 706.

Following entry into the test mode, the toroidal bladder 724 is automatically inflated to its maximum target air pressure, e.g., 15 psi, providing a horizontal stabilized balance platform 706 on which the subject may safely mount. Under control of the computer, the toroidal bladder may be inflated by one of: an air pressure pump, as shown in FIG. 1B, and a high-pressure reservoir, as shown in FIG. 2B, through a control valve corresponding to one of elements: 142 of FIG. 1B and 242 of FIG. 2B, respectively, to restrain downward tilting of the balance platform and provide greater stability to the balance platform. The clinician may then use keyboard or touch-screen inputs to the computer 764 to select the conventional CTSIB in step 810. At about the same time, the computer 764 activates the array of force transducers 705, which then communicate with the computer 764.

Upon selecting the conventional CTSIB, the monitor 768 may clearly display, for example, "Start conventional test: eyes-open, stable platform—Y/N?" in step 820. The clinician initiates the first test with eyes open on the stabilized balance platform 706 by providing an affirmative binary input, "Y", by the hand-held input device 376 or keyboard or touch-screen inputs to the computer 764. The computer 764 may then display on the monitor 768 and record, for about 30 seconds, the changes to the subject's CoP on the stabilized balance platform 706 with eyes open. Alternatively, the computer 706 may compute an index of stability, where the changes to the subject's CoP are subject to rectification and numerically integrated after removal of any DC bias. If the clinician provides a negative binary input, "N", to the first question, then the system 700 returns to the test mode.

After displaying and recording the tilt information of the first test with eyes open of the conventional CTSIB, the monitor 768 may clearly display, for example, "Start conventional test: eyes-closed, stable platform—Y/N?" in step 830. The clinician initiates the second test with eyes closed on the stabilized balance platform 706 by providing an affirmative binary input, "Y", by the hand-held input device 376 or keyboard or touch-screen inputs to the computer 764. The computer may then display on the monitor 768 and record, for about 30 seconds, the changes to the subject's CoP on the stabilized balance platform 706 with eyes closed, to complete the conventional CTSIB. Alternatively, the computer 764 may compute an index of stability, where the changes to the subject's CoP are subject to rectification and numerically integrated after removal of any DC bias. If the clinician provides a negative binary input, "N", to the second question, then the system 700 returns to the test mode.

Figure 9:
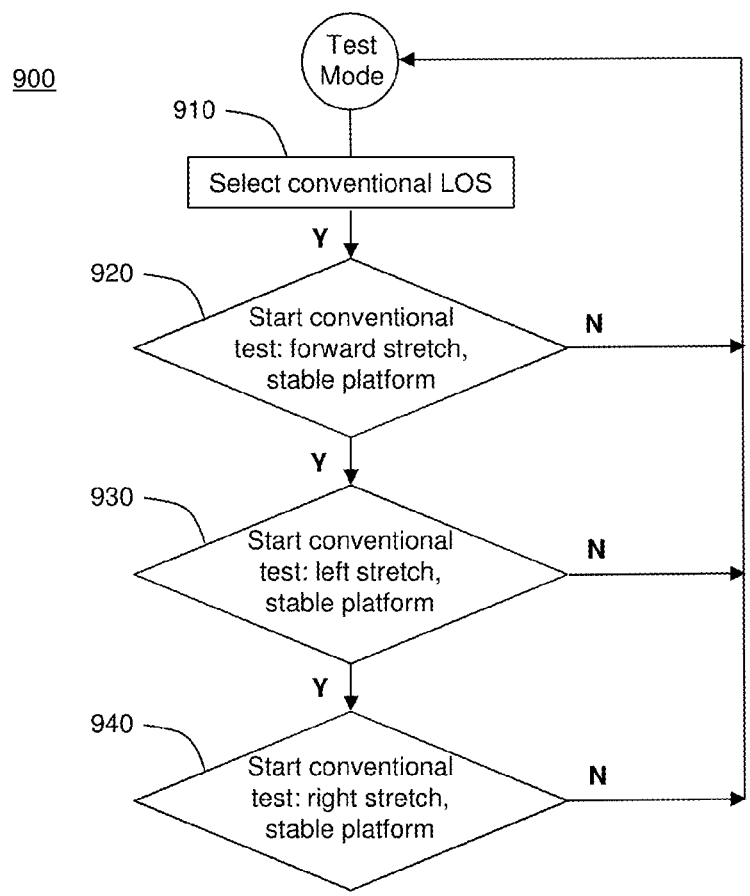
FIG. 9 is a flow chart of a method of performing conventional LOS tests using the structure of FIG. 7B, for clinical assessment of balance, in embodiments herein.

Referring to FIG. 9, an exemplary method 900 of using the system 700 may allow the clinician to select conventional Loss of Stability (LOS) tests that measure, by the array of force transducers 705, changes to the subject's CoP caused by the subject's movements on a horizontal stabilized balance platform 706.

Following entry into the test mode, the toroidal bladder 724 is inflated to its maximum target air pressure, e.g., 15 psi, providing a horizontal stabilized balance platform 706 on which the subject may safely mount. Under control of the computer, the toroidal bladder may be inflated by one of: an air pressure pump, as shown in FIG. 1B, and a high-pressure reservoir, as shown in FIG. 2B, through a control valve corresponding to one of elements: 142 of FIG. 1B and 242 of FIG. 2B, respectively, to restrain downward tilting of the balance platform and provide greater stability to the balance platform. The clinician may then use the keyboard or touch-screen inputs to the computer 764 to select the conventional LOS tests in step 910. At about the same time, the computer 764 activates the array of force transducers 705, which then communicate with the computer 764.

Upon selecting the conventional LOS tests, the monitor 768 may clearly display, for example, "Start conventional test: forward stretch, stable platform—Y/N?" in step 920. The clinician initiates a first forward stretch test on the stabilized balance platform 706 by providing an affirmative binary input, "Y", by the hand-held input device 376 or keyboard or touch-screen inputs to the computer 764. The computer 764 then automatically displays on the monitor 768 and records the changes to the subject's CoP for about 10 seconds. If the clinician provides a negative binary input, "N", to the second question, then the system 700 returns to the test mode.

After displaying and recording the subject's CoP of the conventional forward stretch LOS test on the horizontal stabilized balance platform 706, the monitor 768 may clearly display, for example, "Start conventional test: left stretch, stable platform—Y/N?" in step 930. The clinician may initiate the conventional left stretch LOS test on the horizontal stabilized balance platform 706 by providing an affirmative binary input, "Y", by the hand-held input device 376 or keyboard or touch-screen inputs to the computer 764. The computer then displays and records the changes to the subject's CoP for about 10 seconds. If the clinician provides a negative binary input, "N", to the third question, then the system 700 returns to the test mode.

After displaying and recording the subject's CoP of the conventional left stretch LOS test on the horizontal stabilized balance platform 706, the monitor 768 may clearly display, for example, "Start conventional test: right stretch, stable platform—Y/N?" in step 940. The clinician may initiate the conventional right stretch LOS test on the horizontal stabilized balance platform 706 by providing an affirmative binary input, "Y", by the hand-held input device 376 or keyboard or touch-screen inputs to the computer 764. The computer 764 then displays and records the changes to the subject's CoP for about 10 seconds. If the clinician provides a negative binary input, "N", to the fourth question, then the system 700 returns to the test mode.

Referring back to the cross section of FIG. 7B, the system 700, as configured for measuring tilt information including the direction of tilt in the x-y plane, the degree of tilt along the z-axis, and the calculated rate of change of the degree of tilt along the z-axis, may include a balance platform 706 further including: an upper platform 707 upon which the subject stands; an array of force transducers 705 that are not activated; and a lower platform 703 that supports the array of un-activated force transducers 705. In turn, the lower platform 703 is supported by a ball joint 712 that is disposed on a vertical support 718 underneath the center of the lower platform 703 of the balance platform 706. The vertical support 718 and a toroidal bladder 724, made of an elastic material, are disposed on a base 730. The toroidal bladder 724 encircles the vertical support 718 and supports the lower platform 703 along its periphery.

Under control of the computer 764, the toroidal bladder 724 may be inflated by one of: the air pressure pump 136, as shown in FIG. 1B, and the high-pressure reservoir 272, as shown in FIG. 2B, through a control valve corresponding to one of elements: 142 of FIG. 1B and 242 of FIG. 2B, respectively, to restrain downward tilting of the balance platform 706 and provide greater stability to the balance platform 706. Similarly, deflation of the toroidal bladder 724 under control of the computer 764, by venting to the atmosphere through a control valve, facilitates downward tilting of the lower platform 703 of the balance platform 706, providing lesser stability to the balance platform 706.

An inclinometer 748, e.g., an electronic dual-axis accelerometer, disposed on the underside of the lower platform 703 of the balance platform 706, measures in real time a direction of tilt of the balance platform 706 relative to the supporting ball joint 712 in the horizontal x-y plane and the degree of tilt of the balance platform 706 relative to the z-axis of the supporting ball joint 712, when activated by the computer 764. The computer 764 receives, in real time, the direction of tilt and the degree of tilt of the balance platform 706, computes a rate of change of the degree of tilt, displays this tilt information on a monitor 768 in real time, and stores the tilt information in the subject's computer files.

As described above, before conducting a clinical test, safety requires that the subject mount a stable balance platform 706. Upon entering the test mode of the computer 764 of the system 700, an exemplary embodiment of the invention may automatically inflate the toroidal bladder 724 to a maximum target air pressure of, for example, 15 psi, as measured by an air pressure sensor, corresponding to one of elements: 156 of FIG. 1B and 256 of FIG. 2B. When the air pressure of the toroidal bladder 724 equals the maximum target air pressure, the computer 764 may initiate the modified clinical test, e.g., modified Loss of Stability (LOS) tests, by activating the inclinometer 748, inflating or deflating the toroidal bladder 724 to the target air pressure for the modified clinical test, recording and displaying on the monitor 768 the tilt information including a direction of tilt in the horizontal x-y plane, a degree of tilt along the vertical z-axis, and a calculated rate of change of the degree of tilt along the vertical z-axis, and saving the tilt information, as described above.

Optionally, following automatic inflation of the toroidal bladder 724 to its maximum target air pressure to stabilize the balance platform 706, and prior to activating the inclinometer 748 and initiating a modified clinical test that displays and records the tilt information, the computer 764 may activate the array of force transducers 705 to determine a sensed load, proportional to the weight of the subject, so as to change the degree of stability of the balance platform 606 for subjects of different weights, as described above.

The terminology used herein is for the purpose of describing particular embodiments only and is not intended to be limiting of this disclosure. As used herein, the singular forms "a", "an" and "the" are intended to include the plural forms as well, unless the context clearly indicates otherwise. It will be further understood that the terms "includes" and/or "including," when used in this specification, specify the presence of stated features, integers, steps, operations, elements, and/or components, but do not preclude the presence or addition of one or more other features, integers, steps, operations, elements, components, and/or groups thereof.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system for clinical assessment of balance of a subject on a balance platform with controlled stability, comprising:
   the balance platform supported under its center by a ball joint, the ball joint disposed atop a vertical support, which is disposed on a base;
   a toroidal bladder supporting the balance platform under the periphery of the balance platform, the toroidal bladder encircling the vertical support, and being disposed on the base;
   a high-pressure reservoir maintaining a range of high air pressures, in which a lowest value of the range of high air pressures exceeds that of a maximum target air pressure for the toroidal bladder;
   a control valve connected to the high-pressure reservoir, the toroidal bladder, and the atmosphere;
   an air pressure sensor connected to the toroidal bladder;
   an inclinometer disposed on the underside of the balance platform to measure a direction of tilt of the balance platform in the horizontal x-y plane and a degree of tilt of the balance platform relative to a vertical z-axis in response to the subject's real time movements on the balance platform; and
   a computer:
   receiving an air pressure value from the air pressure sensor;
   receiving measures of the direction of tilt and the degree of tilt of the balance platform;
   sending a first control signal that opens the control valve between the high-pressure reservoir and the toroidal bladder to inflate the toroidal bladder to a target air pressure, restraining downward tilting of the balance platform and providing greater stability to the balance platform, when an air pressure value of the toroidal bladder is less than the target air pressure; and
   sending a second control signal that closes the control valve, when the air pressure sensor senses the target air pressure in the toroidal bladder.

2. The system of claim 1, further comprising:
   an air pump connected to an input valve and a pressure transducer that are connected to the high-pressure reservoir, the pressure transducer measuring a high air pressure of the high-pressure reservoir; and
   the computer:
   further automatically sending a third control signal to activate the air pump and open the input valve, so as to pump air into the high-pressure reservoir, when the pressure transducer measures a high air pressure less than the lowest value of the range of high air pressures, and
   further automatically sending a fourth control signal to de-activate the air pump and close the input valve, when the pressure transducer measures a high air pressure equal to a highest value of the range of high air pressures.

3. The system of claim 2, the computer:
   yet further sending a fifth control signal to the control valve, so as to deflate the toroidal bladder to the atmosphere facilitating downward tilting of the balance platform and providing lesser stability to the balance platform, when the air pressure of the toroidal bladder is greater than the target air pressure, and
   yet further sending the second control signal that closes the control valve, when the air pressure sensor senses the target air pressure in the toroidal bladder.

4. The system of claim 3, the air pressure sensor communicating wirelessly, in real time, air pressures of the toroidal bladder to the computer, and the computer wirelessly communicating, in real time, control signals to inflate or to deflate the toroidal bladder to the target air pressure.

5. The system of claim 1, the target air pressure being input from the computer and corresponding to one or more stages of a clinical test for the assessment of balance.

\* \* \* \* \*